United States Patent [19]
Patterson

[11] Patent Number: 6,093,152
[45] Date of Patent: Jul. 25, 2000

[54] PULSE WIDTH MODULATION VALVE CONTROL FOR VITAL SIGN MONITORS

[75] Inventor: Paul D. Patterson, Portland, Oreg.

[73] Assignee: Protocol Systems, Inc., Beaverton, Oreg.

[21] Appl. No.: 09/183,488

[22] Filed: Oct. 30, 1998

Related U.S. Application Data

[60] Provisional application No. 60/064,397, Oct. 30, 1997.
[51] Int. Cl.$^7$ ............................................. A61B 5/02
[52] U.S. Cl. ............................................. 600/495; 600/490
[58] Field of Search .................................. 600/490–499, 600/500, 501

[56] References Cited

U.S. PATENT DOCUMENTS

| | | | |
|---|---|---|---|
| 4,116,230 | 9/1978 | Gorelick | 600/495 |
| 4,969,466 | 11/1990 | Brooks | 600/494 |
| 5,224,484 | 7/1993 | Newell | 600/493 |
| 5,337,751 | 8/1994 | Newell et al. | 600/495 |

*Primary Examiner*—Cary O'Connor
*Assistant Examiner*—Navin Natnithithadha
*Attorney, Agent, or Firm*—Kolisch Hartwell Dickinson McCormack & Heuser

[57] ABSTRACT

A method for measuring a patient's blood pressure involves using a patient-applied cuff operably connected to an electronically controlled blood pressure monitor that includes a pump. The method includes controlling pressure in the cuff by inflating the cuff to a suprasystolic pressure, and step-wise deflating of the cuff to acquire blood-pressure data from the patient. The improvement includes using pulse-width modulation data to enhance control of cuff pressure.

1 Claim, No Drawings

PULSE WIDTH MODULATION VALVE CONTROL FOR VITAL SIGN MONITORS

CROSS-REFERENCE TO RELATED APPLICATIONS

This application claims priority from U.S. Provisional Patent Application Ser. No. 60/064,397 entitled "PULSE WIDTH MODULATION VALVE CONTROL FOR VITAL SIGN MONITORS" which was filed on Oct. 30,1997.

FIELD OF INVENTION

The present invention relates to vital signs monitors and particularly to non-invasive blood pressure monitors.

BACKGROUND AND SUMMARY OF THE INVENTION

Among many sub-fields in the general field of medicine, the obtaining of vessel-occluded vital-signs information has gained increasing versatility with the steady arrival of new automated and semiautomated systems. An area within this sub-field which has drawn much creative attention in recent years is that involving non-invasive blood pressure (NIPB) measuring systems and techniques, and a preferred embodiment of the present invention is disclosed in the NIBP setting. In recent medical-advancement history, a leading contributor in this arena has been Protocol Systems Inc. of Beaverton, Oreg., and the following several issued U.S. patents, each of which is incorporated herein by reference, evidence some of the contributions made by this innovative company: U.S. Pat. No. 4,889,133 to Nelson et al., U.S. Pat. No. 4,949,710 to Dorsett et al., and U.S. Pat. No. 5,339,822 to Taylor et al.

Preliminarily, it should be understood that vital signs monitors are monitors with the capability of measuring various vital signs of a patient including blood pressure, pulse rate, saturated oxygen levels, etc. Blood pressure monitors are monitors that are designed to perform only NIBP. The present invention is usable with vital signs monitors or blood pressure monitors.

Despite the many advances which have been contributed by Protocol and by others in the NIBP field, there has continued to be a need for the payment of further attention to issues involving patient safety and comfort, and to acquisition of blood-pressure data in an independent and precisely controlled fashion which allows for the gathering of such data as rapidly as possible, without having to deal with distracting anomalies created by so-called artifacts in the blood-pressure-signal data stream.

One area where there is a particular need for improvement relates to necessary control of pressure existing in patient-applied blood pressure cuffs. Current NIBP devices use three types of valves for pressure control on patient-applied blood pressure cuffs. The typical method is to turn on a pump to inflate the applied cuff to a predetermined pressure. Controlling this pressure inflation rate and limit is performed by independent pump control, independent valve control or both. The deflation of the cuff pressure is performed by valve control or by forcing air through a specific size port small enough to allow cuff deflation to be at a specific, desired rate. On inflation, pulse width modulation on the pump allows inflation control to be maintained at specific or varied rates.

Another method is to turn on the pump and force the air through a variable orifice similar to a servo valve. The current applied to the valve varies the opening of the valve which controls the inflation rate. On inflation, the pressure in the cuff decreases in either a step bleed or linear bleed manner. Step bleed is performed by opening a valve long enough for the pressure in the cuff to drop a predetermined amount. For example, the pressure in the cuff drops 8 mmHg every time the valve is opened until the pressure in the cuff has reduced to some predetermined level. Then the cuff pressure is rapidly reduced by full opening of the valve.

Linear bleed is performed by using a servo valve or a piezo electric valve. The servo valve uses current control to vary the opening of the valve orifice. When the cuff has reached the target pressure, the opening of the servo valve is controlled so the deflation rate maintains a predetermined deflation profile. The piezo electric valve performs in a similar manner except the control of the valve opening is done by varying the voltage applied to the valve.

The Servo or proportional control valves used in the linear bleed method are expensive and are relatively power hungry. Piezo electric valves are also limited to a narrow temperature range for operation. This range is smaller than the band specified by the NIBP device. For example, 100° F. is a temperature in which a patient could be exposed to, but the piezo electric valve will not function properly.

DETAILED DESCRIPTION OF THE PREFERRED EMBODIMENT

AND

THE PREFERRED MANNER OF PRACTICING THE INVENTION

The present invention proposes using pulse width modulation on a digital valve to control the inflation and deflation of the applied cuff. For a description of the design of a preferred NIBP system including an electronically-controlled blood pressure monitor that includes a pump and a patient-applied cuff, see the above-identified patents incorporated by reference. In addition to those disclosures, the invention involves use of a digital valve to perform the step bleed function. Typically that valve is either fully closed or it is fully open. Digital valves are available and less expensive than other valves. However, there exists no information about pulse width modulation data for these valves. Representative manufacturers of digital valves usable in connection with the present invention are: SMC, Numatech, The Lee Company, Pneutronics, Electrodyne, Clippard instruments, Oken Seiko, Humphrey Products.

Driving the valve with a variable duty cycle and a variable frequency, the flow through the valve can be controlled to follow any flow requirement. For example, if the flow requirement is to start relatively high then gradually decrease, the valve can be controlled to match the desired flow curve. Testing has identified that when the fluid supply to the valve is connected to a normally open port, the flow increases as the duty cycle increases and the flow decreases as the drive frequency increases. Flow is inversely proportional to the drive frequency and proportional to the duty cycle. The information described in this paragraph is an example of the type of information that can be used to provide pulse width modulation data from an electronically-controlled blood pressure monitor. When using this information in connection with evaluating digital valve performance, virtually any desired flow curve can be matched by analyzing pulse width modulation data.

Accordingly, the invention involves controlling NIBP cuff pressure utilizing pulse width modulation data.

While the present invention has been shown and described with reference to the foregoing preferred embodiment, it will be apparent to those skilled in the art that other changes in form and detail may be made therein without departing from the spirit and scope of the invention as described further below.

I claim:

1. A method for measuring a patient's blood pressure that involves using a patient-applied cuff operably connected to an electronically controlled blood pressure monitor including a pump, controlling pressure in the cuff by inflating the cuff to a suprasystolic pressure, and step-wise deflating of the cuff to acquire blood-pressure data from the patient, the improvement comprising:

choosing a digital valve to control inflating and deflating of the patient-applied cuff coupling the valve to the pump and including a port in the valve that is set to be open;

determining that fluid flow increases as the duty cycle of the pump increases, that fluid flow decreases as the drive frequency of the pump increases, and that flow is inversely proportional to the drive frequency of the pump and proportional to the duty cycle of the pump;

evaluating the performance of the digital valve; and using the information from the determining and evaluating steps to select a desired fluid flow curve for the pump.

* * * * *